US007651536B2

(12) United States Patent
Cottard et al.

(10) Patent No.: US 7,651,536 B2
(45) Date of Patent: Jan. 26, 2010

(54) COMPOSITION FOR DYEING OF KERATIN FIBERS, COMPRISING 2,3-DIAMINO-6,7-DIHYDRO-1H,5H-PYRAZOLO[1,2-A]PYRAZOL-1-ONE, AT LEAST ONE OXIDATION BASE CHOSEN FROM PARA-PHENYLENEDIAMINE AND PARA-TOLYLENEDIAMINE, AND A SUBSTITUTED META-AMINOPHENOL

(75) Inventors: François Cottard, Courbevoie (FR); Patricia Desenne, Bois Colombes (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/812,603

(22) Filed: Jun. 20, 2007

(65) Prior Publication Data

US 2008/0016627 A1 Jan. 24, 2008

Related U.S. Application Data

(60) Provisional application No. 60/818,273, filed on Jul. 5, 2006.

(30) Foreign Application Priority Data

Jun. 20, 2006 (FR) .................................. 06 52557

(51) Int. Cl.
A61Q 5/10 (2006.01)
C07D 231/44 (2006.01)
(52) U.S. Cl. ........................ 8/405; 8/406; 8/407; 8/408; 8/410; 8/411; 8/412; 8/421; 8/567; 548/369.1
(58) Field of Classification Search .................... 8/405, 8/406, 407, 408, 410, 411, 412, 421, 567; 514/406, 407; 548/369.1
See application file for complete search history.

(56) References Cited

U.S. PATENT DOCUMENTS

| 3,012,884 | A | 12/1961 | de Ramaix et al. |
| 4,003,699 | A | 1/1977 | Rose et al. |
| 4,128,425 | A | 12/1978 | Greenwald |
| RE30,199 | E | 1/1980 | Rose et al. |
| 4,823,985 | A | 4/1989 | Grollier et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,718,731 | A | 2/1998 | Loewe et al. |
| 5,766,576 | A | 6/1998 | Löwe et al. |
| 6,099,592 | A | 8/2000 | Vidal et al. |
| 6,099,593 | A | 8/2000 | Terranova et al. |
| 6,284,003 | B1 | 9/2001 | Rose et al. |
| 6,338,741 | B1 | 1/2002 | Vidal et al. |
| 6,436,151 | B2 | 8/2002 | Cottard et al. |
| 6,645,258 | B2 | 11/2003 | Vidal et al. |
| 6,660,046 | B1 | 12/2003 | Terranova et al. |
| 6,730,789 | B1 | 5/2004 | Birault et al. |
| 7,285,137 | B2 * | 10/2007 | Vidal et al. ........................ 8/405 |
| 7,485,156 | B2 | 2/2009 | Saunier |
| 7,488,355 | B2 | 2/2009 | Saunier |
| 7,488,356 | B2 | 2/2009 | Saunier |
| 2001/0023514 | A1 | 9/2001 | Cottard et al. |
| 2002/0046431 | A1 | 4/2002 | Laurent et al. |
| 2002/0050013 | A1 | 5/2002 | Vidal et al. |
| 2002/0088062 | A1 | 7/2002 | Pratt |
| 2003/0019051 | A9 | 1/2003 | Vidal et al. |
| 2005/0166335 | A1 | 8/2005 | Vidal et al. |
| 2007/0006398 | A1 | 1/2007 | Hercouet |
| 2008/0005853 | A1 | 1/2008 | Cottard et al. |
| 2008/0016627 | A1 | 1/2008 | Cottard et al. |
| 2008/0016628 | A1 | 1/2008 | Cottard et al. |
| 2009/0007347 | A1 | 1/2009 | Cottard et al. |

FOREIGN PATENT DOCUMENTS

| CH | 421 343 | | 9/1966 |
| DE | 1 959 009 | | 12/1970 |
| DE | 23 59 399 | A1 | 6/1975 |
| DE | 38 43 892 | A1 | 6/1990 |
| DE | 41 33 957 | A1 | 4/1993 |
| DE | 195 43 988 | A1 | 5/1997 |
| DE | 196 19 112 | | 11/1997 |
| DE | 101 48 847 | A1 | 5/2003 |
| EP | 0 770 375 | B1 | 5/1997 |
| EP | 0 873 745 | | 10/1998 |

(Continued)

OTHER PUBLICATIONS

STIC Search Report dated Jul. 13, 2008.*
French Search Report for FR 0652557, dated Mar. 9, 2007.
English language abstract of DE 101 48 847 A1, May 10, 2003.
English language abstract of EP 0 770 375 B1, May 2, 1997.
English language abstract of JP 2-19576, Jan. 23, 1990.

(Continued)

Primary Examiner—Eisa B Elhilo
(74) Attorney, Agent, or Firm—Finnegan, Henderson, Farabow, Garrett & Dunner, LLP

(57) ABSTRACT

Disclosed herein is a composition for dyeing keratin fibers, comprising at least one first oxidation base chosen from 2,3-diamino-6,7-dihydro-1H,5H-pyrazolo[1,2-a]pyrazol-1-one and the addition salts thereof, at least one second coupler chosen from para-phenylenediamine, para-tolylenediamine, and the addition salts thereof, and at least one coupler chosen from substituted meta-aminophenols, wherein the first coupler/first oxidation base mole ratio is greater than 1, the first oxidation base/second oxidation base mole ratio ranges from 0.5 to 1.5, and the molar amount of the first oxidation base is greater than or equal to $2.5 \times 10^{-3}$ mol per 100 g of composition. Also disclosed herein is a dyeing process comprising applying such a composition to the keratin fibers. The compositions of the present disclosure may make it possible to obtain a strong, aesthetic, sparingly selective, and/or fast coloration of keratin fibers in visible deep red shades. The composition may also allow a strong coloration to be obtained at neutral pH.

14 Claims, No Drawings

FOREIGN PATENT DOCUMENTS

| | | |
|---|---|---|
| EP | 1 250 909 | 10/2002 |
| EP | 1 550 656 A1 * | 6/2005 |
| EP | 1 550 656 A1 | 7/2005 |
| FR | 2 586 913 A1 | 3/1987 |
| FR | 2 733 749 A1 | 11/1996 |
| FR | 2 750 048 A1 | 12/1997 |
| FR | 2 801 308 A1 | 5/2001 |
| FR | 2 886 132 | 12/2006 |
| FR | 2 886 135 | 12/2006 |
| FR | 2 886 136 | 12/2006 |
| FR | 2 886 137 | 12/2006 |
| FR | 2 886 138 | 12/2006 |
| FR | 2 886 139 | 12/2006 |
| FR | 2 886 140 | 12/2006 |
| FR | 2 886 141 | 12/2006 |
| FR | 2 886 142 | 12/2006 |
| FR | 2 902 323 | 12/2007 |
| FR | 2 902 327 | 12/2007 |
| FR | 2 902 328 | 12/2007 |
| GB | 1 005 233 | 9/1965 |
| GB | 1 026 978 | 4/1966 |
| GB | 1 153 196 | 5/1969 |
| GB | 1 486 576 | 9/1977 |
| JP | 2-19576 | 1/1990 |
| JP | 5-163124 | 6/1993 |
| JP | 2002-535312 | 10/2002 |
| WO | WO 94/08969 | 4/1994 |
| WO | WO 94/08970 | 4/1994 |
| WO | WO 96/15765 | 5/1996 |

OTHER PUBLICATIONS

English language abstract of JP 5-163124, Jun. 29, 1993.
Co-pending U.S. Appl. No. 10/999,999, filed Dec. 1, 2004.
Co-pending U.S. Appl. No. 11/812,610, filed Jun. 20, 2007.
Co-pending U.S. Appl. No. 11/812,616, filed Jun. 20, 2007.
Co-pending U.S. Appl. No. 11/898,438, filed Sep. 12, 2007.
Co-pending U.S. Appl. No. 11/987,450, filed Nov. 30, 2007.
Co-pending U.S. Appl. No. 11/987,451, filed Nov. 30, 2007.
English language Abstract of DE 1 959 009, dated Dec. 3, 1970.
English language Abstract of DE 196 19 112, dated Nov. 13, 1997.
English language Abstract of EP 0 873 745, dated Oct. 28, 1998.
English language Abstract of EP 1 250 909, dated Oct. 23, 2002.
English language Abstract of FR 2 886 135, dated Dec. 1, 2006.
English language Abstract of FR 2 886 136, dated Dec. 1, 2006.
English language Abstract of FR 2 886 140, dated Dec. 1, 2006.
English language Abstract of FR 2 886 141, dated Dec. 1, 2006.
English language Abstract of FR 2 886 142, dated Dec. 1, 2006.
European Search Report for EP 07 12 1666, dated Apr. 2, 2008.
French Search Report for FR 06/52549, dated Mar. 6, 2007.
French Search Report for FR 06/52558, dated Mar. 9, 2007.
French Search Report for FR 06/55213, dated Nov. 30, 2006.
French Search Report for FR 06/55214, dated Jul. 25, 2007.
Helvetica Chimica Acta., vol. XXXIII, Fasciculus V (1950), No. 152, pp. 1183-1194.
Morissette et al., Advanced Drug Delivery Reviews, 2004, 56, pp. 275-300.
Notice of Allowance mailed Jun. 26, 2007, in co-pending U.S. Appl. No. 10/999,999.
Notice of Allowance mailed Mar. 9, 2007, in co-pending U.S. Appl. No. 10/999,999.
Notice of rejection in counterpart Japanese Application No. 2004-348020, mailed Dec. 6, 2005.
Notice of rejection in counterpart Japanese Application No. 2004-348020, mailed Jan. 29, 2008.
Office Action mailed Apr. 14, 2009, in co-pending U.S. Appl. No. 11/812,616.
Office Action mailed Apr. 16, 2009, in co-pending U.S. Appl. No. 11/812,610.
Office Action mailed Apr. 27, 2009, in co-pending U.S. Appl. No. 11/987,451.
Office Action mailed Aug. 15, 2008, in co-pending U.S. Appl. No. 11/812,616.
Office Action mailed Mar. 2, 2009, in co-pending U.S. Appl. No. 11/898,438.
Office Action mailed Mar. 24, 2009, in co-pending U.S. Appl. No. 11/812,603.
Office Action mailed May 1, 2009, in co-pending U.S. Appl. No. 11/987,450.
Office Action mailed Oct. 27, 2008, in co-pending U.S. Appl. No. 11/987,450.
Office Action mailed Oct. 28, 2008, in co-pending U.S. Appl. No. 11/987,451.
STIC Search Report for U.S. Appl. No. 10/999,999, dated Dec. 13, 2006.
STIC Search Report for U.S. Appl. No. 11/812,603, dated Jul. 13, 2008.
STIC Search Report for U.S. Appl. No. 11/812,610, dated Jul. 31, 2008.
Vippagunta, S.R., "Crystalline Solids," Advanced Drug Delivery Reviews, 2001, 48, pp. 3-26.

* cited by examiner

COMPOSITION FOR DYEING OF KERATIN FIBERS, COMPRISING 2,3-DIAMINO-6,7-DIHYDRO-1H,5H-PYRAZOLO[1,2-A]PYRAZOL-1-ONE, AT LEAST ONE OXIDATION BASE CHOSEN FROM PARA-PHENYLENEDIAMINE AND PARA-TOLYLENEDIAMINE, AND A SUBSTITUTED META-AMINOPHENOL

This application claims benefit of U.S. Provisional Application No. 60/818,273, filed Jul. 5, 2006, the contents of which are incorporated herein by reference. This application also claims benefit of priority under 35 U.S.C. § 119 to French Patent Application No. FR 06/52557, filed Jun. 20, 2006, the contents of which are also incorporated herein by reference.

Disclosed herein is a composition for dyeing keratin fibers, for example, human keratin fibers such as the hair, comprising at least one first oxidation base chosen from 2,3-diamino-6,7-dihydro-1H,5H-pyrazolo[1,2-a]pyrazol-1-one, at least one second oxidation base chosen from para-phenylenediamine and para-tolylenediamine, and at least one first coupler chosen from substituted meta-aminophenol.

It is known practice to dye keratin fibers, for instance, human keratin fibers such as the hair, with dye compositions comprising oxidation dye precursors, for example, ortho- and para-phenylenediamines, ortho- and para-aminophenols, and heterocyclic compounds such as diaminopyrazole derivatives, pyrazolo[1,5-a]pyrimidine derivatives, pyrimidine derivatives, pyridine derivatives, indole derivatives, and indoline derivatives, which are generally known as oxidation bases. Oxidation dye precursors, or oxidation bases, are colorless or weakly colored compounds that, when combined with oxidizing products, can give rise to dyes or colored compounds via a process of oxidative condensation. Permanent colorations are thus obtained.

It is also known that the shades obtained with these oxidation bases may be varied by combining them with couplers or coloration modifiers, the latter being chosen, for example, from meta-phenylenediamines, meta-aminophenols, meta-hydroxyphenols, and certain heterocyclic compounds.

The variety of molecules available as oxidation bases and couplers allows a wide range of colors to be obtained.

The use of oxidation bases such as para-phenylenediamine and para-aminophenol derivatives allows a quite broad range of colors to be obtained at basic pH without, however, achieving shades with good chromaticity, while at the same time giving the hair excellent properties in terms of strength of color, uniformity of the color, and/or fastness with respect to external agents.

However, the use of these bases at neutral pH does not allow a varied range of shades to be produced, for example, for warm shades such as reds and oranges.

Thus, disclosed herein are novel compositions for dyeing keratin fibers that may make it possible to obtain a strong, chromatic, aesthetic, and/or sparingly selective coloration, and in at least one embodiment, visible deep red shades, which shows good resistance to the various attacking factors to which the hair may be subjected, such as shampoo, light, sweat, and/or permanent reshaping operations.

Disclosed herein is thus a composition for dyeing keratin fibers, comprising, in a medium suitable for dyeing:

at least one first oxidation base chosen from 2,3-diamino-6,7-dihydro-1H,5H-pyrazolo[1,2-a]pyrazol-1-one of formula (I) below, and the addition salts thereof:

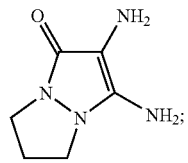

at least one second oxidation base chosen from para-phenylenediamine and para-tolylenediamine, and the addition salts thereof; and at least one first coupler chosen from substituted meta-aminophenols of formula (II) below, and the addition salts thereof:

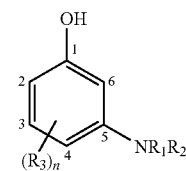

wherein:

$R_1$ and $R_2$, which may be identical or different, are chosen from hydrogen; alkyl radicals; monohydroxyalkyl radicals; polyhydroxyalkyl radicals; and monoaminoalkyl radicals; or $R_1$ and $R_2$ may form, together with the nitrogen atom to which they are attached, a saturated or unsaturated, 5- to 7-membered cyclic group comprising at least one heteroatom, which may be unsubstituted or substituted with at least one radical chosen from carboxyl, carboxamido, hydroxyl, amino, monoalkylamino, and dialkylamino radicals, and alkyl radicals optionally substituted with at least one radical chosen from hydroxyl, amino, monoalkylamino, and dialkylamino radicals;

$R_3$, which may be identical or different, is chosen from halogen atoms; alkyl radicals; alkoxy radicals; monohydroxyalkyl radicals; polyhydroxyalkyl radicals; monohydroxyalkoxy radicals; and polyhydroxyalkoxy radicals;

n is an integer ranging from 0 to 4;

with the proviso that when n is equal to 0, then at least one of the radicals $R_1$ and $R_2$ is not hydrogen; and wherein the at least one first coupler and the at least one first oxidation base are present in a mole ratio of greater than 1, the at least one first oxidation base and the at least one second oxidation base are present in a mole ratio ranging from 0.5 to 1.5, and the molar amount of the first oxidation base is greater than or equal to $2.5 \times 10^{-3}$ mol per 100 g of composition.

The composition of the present disclosure may allow keratin fibers to be colored in visible deep red shades, for instance, a coloration, on natural or permanent-waved grey hair containing 90% white hairs having, according to the CIELab notation, a value for L* of less than or equal to 50, a value for a* ranging from 10 to 25, a value for b* ranging from 3 to 25, and a ratio b*/a* ranging from 0.3 to 1, for example, from 0.3 to 0.7.

The composition of the present disclosure may also make it possible to obtain a strong, aesthetic, and/or sparingly selective coloration that shows good resistance to the various attacking factors to which the hair may be subjected, such as shampoo, light, sweat, and/or permanent reshaping operations. The composition of the present disclosure furthermore may make it possible to obtain an intense coloration at neutral pH.

Also disclosed herein is a process for dyeing keratin fibers comprising applying a composition of the present disclosure to the keratin fibers.

Also disclosed herein is a dyeing kit comprising at least one first compartment containing a dye composition comprising at least one first oxidation base chosen from 2,3-diamino-6, 7-dihydro-1H,5H-pyrazolo[1,2-a]pyrazol-1-one and addition salts thereof, at least one second oxidation base chosen from para-phenylenediamine and para-tolylenediamine, and at least one coupler chosen from substituted meta-aminophenols, and at least one second compartment containing at least one oxidizing agent.

The CIELab notation used in the context of the present disclosure defines a colorimetric space in which each color is defined by three parameters (L*, a*, b*). The parameter L* reflects the lightness of the color, the value L* being equal to 0 for black and equal to 100 for absolute white. The higher the value of L*, the less intense the coloration. The parameter a* corresponds to the axis of the green/red antagonist pair. The parameter b* corresponds to the axis of the blue/yellow antagonist pair.

Unless otherwise indicated, the limits of the ranges of values given in the context of the present disclosure are included in these ranges.

As used herein, the term "alkyl radical" means, unless otherwise indicated, linear or branched $C_1$-$C_{10}$, for example, $C_1$-$C_6$, or $C_1$-$C_4$, alkyl radicals, such as methyl, ethyl, propyl, isopropyl, isobutyl, tert-butyl, pentyl, and hexyl radicals.

As used herein, the term "heteroatom" denotes an atom chosen from oxygen, nitrogen, sulfur, and phosphorus.

As used herein, the term "halogen" denotes an atom chosen from chlorine, bromine, iodine, and fluorine.

According to one embodiment of the present disclosure, $R_1$ and $R_2$, which may be identical or different, are chosen from hydrogen; alkyl radicals, for example, methyl and ethyl radicals; and monohydroxyalkyl radicals, for example, β-hydroxyethyl and γ-hydroxypropyl radicals; or $R_1$ and $R_2$ may form, together with the nitrogen atom to which they are attached, a ring chosen from pyrrolidine, piperidine, homopiperidine, piperazine, homopiperazine, and morpholine heterocycles; the rings possibly being substituted with at least one radical chosen from hydroxyl, amino, mono($C_1$-$C_2$)alkylamino, di($C_1$-$C_2$)alkylamino, carboxyl, and carboxamido radicals, and $C_1$-$C_4$ alkyl radicals optionally substituted with at least one radical chosen from hydroxyl, amino, mono($C_1$-$C_2$)alkylamino, and di($C_1$-$C_2$)alkylamino radicals, and in one embodiment, a ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(β-hydroxyethyl)-aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, N-(2-hydroxyethyl)homopiperazine, piperazine, 4-methylpiperazine, 4-ethylpiperazine, 4-(β-hydroxyethyl)piperazine, and morpholine, and in another embodiment, a ring chosen from pyrrolidin-1-yl; piperidin-1-yl; piperazin-1-yl; 4-methylpiperazin-1-yl; 4-ethylpiperazin-1-yl; 4-(β-hydroxyethyl)piperazin-1-yl; and morpholin-4-yl.

According to one embodiment of the present disclosure, $R_3$ is chosen from halogen atoms, alkyl radicals, alkoxy radicals, and monohydroxyalkoxy radicals. For example, $R_3$ may be chosen from chlorine, methyl radicals, methoxy radicals, and β-hydroxyethyloxy radicals.

According to another embodiment of the present disclosure, n is an integer ranging from 0 to 2, for example, n may be equal to 1 or 2. In a further embodiment, when n is equal to 1, $R_3$ may be in position 2 and when n is equal to 2, $R_3$ may be in positions 2 and 4 or in positions 2 and 6.

Non-limiting examples of substituted meta-aminophenols of formula (II) that are useful in the context of the present disclosure include 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 6-chloro-2-methyl-5-aminophenol, 5-amino-2,4-dimethoxyphenol, 5-(γ-hydroxypropylamino)-2-methylphenol, 3-dimethylaminophenol; 2-methyl-5-dimethylaminophenol; 2-ethyl-5-dimethylaminophenol; 2-methoxy-5-dimethylaminophenol; 2-ethoxy-5-dimethylaminophenol; 2-(β-hydroxyethyl)-5-dimethylaminophenol; 3-diethylaminophenol; 2-methyl-5-diethylaminophenol; 2-ethyl-5-diethylaminophenol; 2-methoxy-5-diethylaminophenol; 2-ethoxy-5-diethylaminophenol; 2-(β-hydroxyethyl)-5-diethylaminophenol; 3-di(β-hydroxyethyl)aminophenol; 2-methyl-5-di(β-hydroxyethyl)amino-phenol; 2-ethyl-5-di(β-hydroxyethyl)aminophenol; 2-methoxy-5-di(β-hydroxyethyl)amino-phenol; 2-ethoxy-5-di(β-hydroxyethyl)aminophenol; 2-(β-hydroxyethyl)-5-di(β-hydroxyethyl)aminophenol; 3-pyrrolidin-1-ylphenol; 2-methyl-5-pyrrolidin-1-ylphenol; 2-ethyl-5-pyrrolidin-1-ylphenol; 2-methoxy-5-pyrrolidin-1-ylphenol; 2-ethoxy-5-pyrrolidin-1-ylphenol; 2-(β-hydroxyethyl)-5-pyrrolidin-1-ylphenol; 3-piperidin-1-ylphenol; 2-methyl-5-piperidin-1-ylphenol; 2-ethyl-5-piperidin-1-ylphenol; 2-methoxy-5-piperidin-1-ylphenol; 2-ethoxy-5-piperidin-1-ylphenol; 2-(β-hydroxyethyl)-5-piperidin-1-ylphenol; 3-piperazin-1-ylphenol; 2-methyl-5-piperazin-1-ylphenol; 2-ethyl-5-piperazin-1-ylphenol; 2-methoxy-5-piperazin-1-ylphenol; 2-ethoxy-5-piperazin-1-ylphenol; 2-(β-hydroxyethyl)-5-piperazin-1-ylphenol; 3-(4-methylpiperazin-1-yl)phenol; 2-methyl-5-(4-methylpiperazin-1-yl)phenol; 2-ethyl-5-(4-methylpiperazin-1-yl)phenol; 2-methoxy-5-(4-methylpiperazin-1-yl)phenol; 2-ethoxy-5-(4-methylpiperazin-1-yl)phenol; 2-(β-hydroxyethyl)-5-(4-methylpiperazin-1-yl)phenol; 3-(4-ethylpiperazin-1-yl)phenol; 2-methyl-5-(4-ethylpiperazin-1-yl)phenol; 2-ethyl-5-(4-ethylpiperazin-1-yl)phenol; 2-methoxy-5-(4-ethylpiperazin-1-yl)phenol; 2-ethoxy-5-(4-ethylpiperazin-1-yl)phenol; 2-(β-hydroxyethyl)-5-(4-ethylpiperazin-1-yl)phenol; 3-(4-(β-hydroxyethyl)piperazin-1-yl)phenol; 2-methyl-5-(4-(β-hydroxyethyl)piperazin-1-yl)phenol; 2-ethyl-5-(4-(β-hydroxyethyl)piperazin-1-yl)phenol; 2-methoxy-5-(4-(β-hydroxyethyl)piperazin-1-yl)phenol; 2-ethoxy-5-(4-(β-hydroxyethyl)piperazin-1-yl)phenol; 2-(β-hydroxyethyl)-5-(4-(β-hydroxyethyl)piperazin-1-yl)phenol; 3-morpholin-4-ylphenol; 2-methyl-5-morpholin-4-ylphenol; 2-ethyl-5- morpholin-4-ylphenol; 2-methoxy-5-morpholin-4-ylphenol; 2-ethoxy-5-morpholin-4-ylphenol; and 2-(β-hydroxyethyl)-5-morpholin-4-ylphenol.

According to one embodiment, the substituted meta-aminophenols of formula (II) may be chosen from 5-N-(β-hydroxyethylamino)-2-methylphenol, 5-amino-2-methylphenol, and 6-chloro-2-methyl-5-aminophenol.

In the composition in accordance with the present disclosure, the first coupler/first oxidation base mole ratio is greater than 1, for example, the ratio may range from 2 to 5.

In the composition in accordance with the present disclosure, the first oxidation base/second oxidation base mole ratio ranges from 0.5 to 1.5, for example, from 0.7 to 1.3.

The dye composition of the invention may further comprise at least one additional oxidation base, other than those that are described above, conventionally used for the dyeing of keratin fibers.

The composition of the present disclosure may comprise, for example, at least one additional oxidation base chosen from para-phenylenediamines other than para-phenylenediamine and para-tolylenediamine and the addition salts thereof, such as bis(phenyl)alkylenediamines, para-aminophenols, bis-para-aminophenols, ortho-amino-phenols, ortho-phenylenediamines, and heterocyclic bases other than 2,3-diamino-6,7-dihydro-1H,5H-pyrazolo[1,2-a]pyrazol-1-one and the addition salts thereof.

Examples of para-phenylenediamines include, but are not limited to, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof.

Suitable para-phenylenediamines may be chosen, for example, from 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the addition salts thereof.

Non-limiting examples of bis(phenyl)alkylenediamines include N,N'-bis(β-hydroxyethyl)-N,N'-bis(4'-aminophenyl)-1,3-diaminopropanol, N,N'-bis-(β-hydroxyethyl)-N,N'-bis(4-minophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane, and the addition salts thereof.

Examples of para-aminophenols that may be used as oxidation bases in the dye compositions in accordance with the include, but are not limited to, the compounds of formula (III) below, and the addition salts thereof:

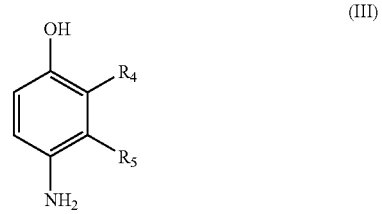

(III)

wherein:
R$_4$ is chosen from hydrogen; halogen atoms; alkyl radicals; monohydroxyalkyl radicals; alkoxyalkyl radicals; aminoalkyl radicals; and hydroxyalkylaminoalkyl radicals;
R$_5$ is chosen from hydrogen; halogen atoms; alkyl radicals; monohydroxyalkyl radicals; polyhydroxyalkyl radicals; aminoalkyl radicals; cyanoalkyl radicals; and alkoxyalkyl radicals;
wherein at least one of the radicals R$_4$ and/or R$_5$ is hydrogen.

Non-limiting examples of the para-aminophenols of formula (III) above include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the addition salts thereof.

Suitable ortho-aminophenols may be chosen, for example, from 2-aminophenol, 2-amino-5-methylphenol, 2-amino-6-methylphenol, 5-acetamido-2-aminophenol, and the addition salts thereof.

Examples of heterocyclic bases include, but are not limited to, pyridine derivatives, pyrimidine derivatives, and pyrazole derivatives.

Suitable pyridine derivatives may be chosen, for example, from the compounds described in British Patent Nos. 1 026 978 and 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diamino-pyridine, and the addition salts thereof.

Other examples of pyridine oxidation bases include, but are not limited to, 3-aminopyrazolo[1,5-a]pyridine oxidation bases and the addition salts thereof described, for example, in French Patent Application No. 2 801 308, such as, pyrazolo[1,5-a]pyrid-3-ylamine; 2-acetylaminopyrazolo[1,5-a]pyrid-3-ylamine; 2-morpholin-4-ylpyrazolo-[1,5-a]pyrid-3-ylamine; 3-aminopyrazolo[1,5-a]pyridine-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-yl-pyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxy-ethyl)amino]ethanol; 2-[(3-aminopyrazolo[1,5- a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol, and the addition salts thereof.

Non-limiting examples of pyrimidine derivatives include the compounds described, for example, in German Patent No. 2 359 399; Japanese Patent Application No. 88-169 571; Japanese Patent No. 05-63 124; European Patent No. 0 770 375, and International Patent Application Publication No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. 2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, the addition salts thereof, and the tautomeric forms thereof, when a tautomeric equilibrium exists.

Suitable pyrazole derivatives may be chosen, for example, from the compounds described in German Patent Nos. 3 843 892 and 4 133 957, International Patent Application Publication Nos. WO 94/08969 and WO 94/08970, French Patent Application No. 2 733 749, and German Patent Application No. 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1methyl-4-methylaminopyrazole, 3,5-diamino-4-(β-hydroxyethyl)amino-1-methylpyrazole, and the addition salts thereof.

According to one embodiment, the composition in accordance with the present disclosure comprises at least one additional oxidation base chosen from para-aminophenols. According to another embodiment, the composition in accordance with the present disclosure comprises at least one additional oxidation base chosen from para-aminophenol and the addition salts thereof.

The dye composition of the present disclosure may further comprise at least one additional coupler, other than those described above, conventionally used for dyeing keratin fibers.

The composition of the present disclosure may comprise, for example, at least one additional coupler chosen from meta-phenylenediamines, meta-aminophenols other than the meta-aminophenols of formula (II) and the addition salts thereof, meta-diphenols, naphthalene-based couplers, and heterocyclic couplers.

Examples of suitable additional couplers include, but are not limited to, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1-N-(β-hydroxyethyl)amino-3,4-methylenedioxybenzene, 2,6-bis(β-hydroxyethylamino)toluene, and the addition salts thereof.

According to one embodiment, the composition in accordance with the present disclosure comprises at least one additional coupler chosen from 2-amino-3-hydroxypyridine, 1,3-dihydroxy-2-methylbenzene, and the addition salts thereof.

The oxidation base(s) may be present in the dye composition in an amount, for each of them, ranging from 0.001% to 10% by weight, for example, from 0.005% to 6% by weight, relative to the total weight of the dye composition.

The coupler(s) may be present in the dye composition of the present disclosure in an amount, for each of them, ranging from 0.001% to 10% by weight, for example, from 0.005% to 6% by weight, relative to the total weight of the dye composition.

The addition salts of the oxidation bases and of the couplers that may be used in the context of the invention may be chosen, by way of non-limiting example, from acid addition salts, such as hydrochlorides, hydrobromides, sulfates, citrates, succinates, tartrates, lactates, $(C_1-C_4)$alkylsulfonates, tosylates, benzenesulfonates, phosphates, and acetates, and base addition salts, such as sodium hydroxide, potassium hydroxide, ammonia, amines, and alkanolamines.

The medium that is suitable for dyeing, also known as the dye support, is a cosmetic medium chosen from water and mixtures of water and at least one organic solvent to dissolve the compounds which would not be sufficiently soluble in water. Examples of suitable organic solvents include, but are not limited to, $C_1-C_4$ lower alkanols, such as ethanol and isopropanol; polyols and polyol ethers such as 2-butoxyethanol, propylene glycol, propylene glycol monomethyl ether, diethylene glycol monoethyl ether, and monomethyl ether, and aromatic alcohols such as benzyl alcohol and phenoxyethanol, and mixtures thereof.

The at least one organic solvent may be present in the dye composition in an amount ranging from 1% to 40% by weight relative to the total weight of the dye composition, for example, from 5% to 30% by weight.

The dye composition in accordance with the present disclosure may further comprise at least one adjuvant conventionally used in compositions for dyeing the hair, such as anionic, cationic, nonionic, amphoteric, and zwitterionic surfactants and mixtures thereof, anionic, cationic, nonionic, amphoteric, and zwitterionic polymers and mixtures thereof, inorganic and organic thickeners, such as anionic, cationic, nonionic, and amphoteric associative polymeric thickeners, antioxidants, penetrants, sequestrants, fragrances, buffers, dispersants, conditioning agents, for instance, silicones, which may be volatile or non-volatile, and modified or unmodified, film-forming agents, ceramides, preserving agents, and opacifiers.

The at least one adjuvant may be present in the dye composition in an amount, for each of them, ranging from 0.01% to 20% by weight relative to the total weight of the dye composition.

It is to be understood that a person skilled in the art will take care to select the at least one optional additional compound such that the advantageous properties intrinsically associated with the oxidation dye composition in accordance with the present disclosure are not, or are not substantially, adversely affected by the addition envisaged.

The pH of the dye composition in accordance with the present disclosure may range from 3 to 12, for example, from 5 to 11. The pH may be adjusted to the desired value using acidifying or basifying agents usually used in the dyeing of keratin fibers, or using standard buffer systems.

Examples of acidifying agents include, but are not limited to, inorganic and organic acids such as hydrochloric acid, orthophosphoric acid, sulfuric acid, carboxylic acids such as acetic acid, tartaric acid, citric acid, and lactic acid, and sulfonic acids.

Suitable basifying agents include, for example, aqueous ammonia, alkaline carbonates, alkanolamines such as mono-, di-, and triethanolamine and derivatives thereof, sodium hydroxide, potassium hydroxide and compounds of formula (IV) below:

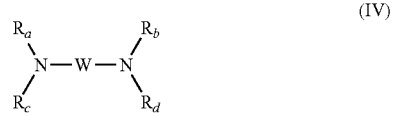

(IV)

wherein:

W is a propylene residue that is unsubstituted or substituted with a hydroxyl group or a $C_1$-$C_4$ alkyl radical; $R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

The dye composition according to the present disclosure may be in various forms, such as liquids, creams, and gels, or in any other form that is suitable for dyeing keratin fibers, such as human hair.

Also disclosed herein is a process comprising applying a composition according to the present disclosure to the fibers, and developing color using an oxidizing agent. The color may be developed at acidic, neutral, or alkaline pH and the oxidizing agent may be added to the composition of the present disclosure just at the time of use, or it may be used starting with an oxidizing composition containing it, which may be applied simultaneously or sequentially to the composition of the present disclosure. In at least one embodiment, the coloration is developed at neutral pH.

According to one embodiment, the composition according to the present disclosure is mixed, for instance, at the time of use, with a composition containing, in a medium that is suitable for dyeing, at least one oxidizing agent, this oxidizing agent being present in an amount that is sufficient to develop a coloration. The mixture obtained is then applied to the keratin fibers. After a leave-on time ranging from 3 to 50 minutes, for example, 5 to 30 minutes, the keratin fibers are rinsed, washed with shampoo, rinsed again, and then dried.

Examples of oxidizing agents conventionally used for the oxidation dyeing of keratin fibers include, but are not limited to, hydrogen peroxide, urea peroxide, alkali metal bromates, persalts such as perborates and persulfates, peracids and oxidase enzymes, such as peroxidases, 2-electron oxidoreductases such as uricases, and 4-electron oxygenases, for instance, laccases. According to one embodiment, the at least one oxidizing agent is hydrogen peroxide.

The oxidizing composition may also comprise at least one adjuvant conventionally used in compositions for dyeing the hair and as defined above.

The pH of the oxidizing composition containing the at least one oxidizing agent is such that, after mixing with the dye composition, the pH of the resulting composition applied to the keratin fibers ranges, for example, from 3 to 12, such as from 5 to 11. The pH may be adjusted to the desired value by means of acidifying or basifying agents usually used in the dyeing of keratin fibers and as defined above.

The ready-to-use composition that is finally applied to the keratin fibers may be in various forms, such as liquids, creams, and gels or any other form that is suitable for dyeing keratin fibers, such as human hair.

Further disclosed herein is a multi-compartment dyeing device or "kit", comprising at least one first compartment containing the dye composition of the present disclosure defined above with the exception of the oxidizing agent and at least one second compartment containing at least one oxidizing composition. This device may be equipped with a means for applying the desired mixture to the hair, such as the devices described in French Patent No. 2 586 913.

According to one embodiment, the application of the composition in accordance with the present disclosure on natural or permanent-waved grey hair containing 90% white hairs makes it possible to obtain a coloration having, according to the CIELab notation, a value for L* of less than or equal to 50, a value for a* ranging from 10 to 25, a value for b* ranging from 3 to 25, and a ratio b*/a* ranging from 0.3 to 1, for instance, from 0.3 to 0.7.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

Example 1

Composition 1 below was prepared:

| | |
|---|---|
| Diethylenetriaminepentaacetic acid, pentasodium salt, as an aqueous 40% solution | 2 g |
| Ammonia as an aqueous 20% solution | 12 g |
| Sodium metabisulfite powder | 0.71 g |
| Pure monoethanolamine | 1.35 g |
| Fumed silica of hydrophobic nature | 1.2 g |

-continued

| | |
|---|---|
| 2,3-Diamino-6,7-dihydro-1H,5H-pyrazolo[1,2-a]pyrazol-1-one, 2 CH$_3$—SO$_3$H | 1.87 g |
| 5-Amino-2-methylphenol | 1.96 g |
| Titanium oxide (untreated anatase) coated with polydimethylsiloxane (98/2) | 0.15 g |
| para-Phenylenediamine | 0.77 g |
| Glycol distearate | 2 g |
| Mica-titanium oxide-brown iron oxide (58/37.5/4.5) | 0.5 g |
| Fragrance | 0.5 g |
| Tetramethylhexamethylenediamine/1,3-dichloropropylene polycondensate as an aqueous solution | 3 g |
| Non-stabilized polydimethyldiallylammonium chloride at 40% in water | 5 g |
| Carboxyvinyl polymer synthesized in an ethyl acetate/cyclohexane mixture | 0.6 g |
| Deionized water | 23.64 g |
| Propylene glycol | 7 g |
| Natural lauric acid | 3 g |
| Oxyethylenated lauryl alcohol (12 OE) | 7 g |
| Oxyethylenated decyl alcohol (3 OE) | 10 g |
| Cetylstearyl alcohol (50/50 C16-18) (synthetic origin) | 11.5 g |
| Oxyethylenated oleocetyl alcohol (30 OE) | 4 g |
| Vitamin C: L-ascorbic acid as a fine powder | 0.25 |

At the time of use, 1 part by weight of composition 1 was mixed with 1.5 parts by weight of a 25-volumes hydrogen peroxide solution at pH 2.2. A final pH of 9.6 was obtained.

The mixture obtained was applied to locks of natural or permanent-waved grey hair containing 90% white hairs. After a leave-on time of 20 minutes at room temperature, the locks were rinsed, washed with a standard shampoo, rinsed again, and then dried.

The hair coloration was evaluated visually. A red-chestnut shade was obtained.

The color of the hair was measured using a Minolta CM 2002® spectrocolorimeter (illuminant D65-10° CSI) in the CIELab system.

The results obtained are given in the table below.

| Type of hair | L* | a* | b* |
|---|---|---|---|
| Natural grey | 25.9 | 15.7 | 6.4 |
| Permanent-waved grey | 23.2 | 12.6 | 5.1 |

Example 2

Composition 2 below was prepared:

| | |
|---|---|
| Diethylenetriaminepentaacetic acid, pentasodium salt, as an aqueous 40% solution | 2 g |
| Ammonia as an aqueous 20% solution | 12 g |
| Sodium metabisulfite powder | 0.71 g |
| Pure monoethanolamine | 1.35 g |
| Fumed silica of hydrophobic nature | 1.2 g |
| 2,3-Diamino-6,7-dihydro-1H,5H-pyrazolo[1,2-a]pyrazol-1-one, 2 CH$_3$—SO$_3$H | 1.87 g |
| 5-Amino-2-methylphenol | 1.96 g |
| Titanium oxide (untreated anatase) coated with polydimethylsiloxane (98/2) | 0.15 g |
| para-Phenylenediamine | 0.77 g |
| para-Aminophenol | 0.15 g |
| Glycol distearate | 2 g |
| Mica-titanium oxide-brown iron oxide (58/37.5/4.5) | 0.5 g |
| Fragrance | 0.5 g |
| Tetramethylhexamethylenediamine/1,3-dichloropropylene polycondensate as an aqueous solution | 3 g |

-continued

| | |
|---|---|
| Non-stabilized polydimethyldiallylammonium chloride at 40% in water | 5 g |
| Carboxyvinyl polymer synthesized in an ethyl acetate/cyclohexane mixture | 0.6 g |
| Deionized water | 23.49 g |
| Propylene glycol | 7 g |
| Natural lauric acid | 3 g |
| Oxyethylenated lauryl alcohol (12 OE) | 7 g |
| Oxyethylenated decyl alcohol (3 OE) | 10 g |
| Cetylstearyl alcohol (50/50 C16-18) (synthetic origin) | 11.5 g |
| Oxyethylenated oleocetyl alcohol (30 OE) | 4 g |
| Vitamin C: L-ascorbic acid as a fine powder | 0.25 |

The dyeing procedure was the same as that used in Example 1.

The hair coloration was evaluated visually. A red-light chestnut shade was obtained.

The color of the hair was measured using a Minolta CM 2002® spectrocolorimeter (illuminant D65-10° CSI) in the CIELab system.

The results obtained are given in the table below.

| Type of hair | L* | a* | b* |
|---|---|---|---|
| Natural grey | 25.7 | 15.6 | 7.4 |
| Permanent-waved grey | 23.9 | 14.6 | 6.4 |

What is claimed is:

1. A composition for dyeing keratin fibers, comprising, in a medium suitable for dyeing:

at least one first oxidation base chosen from 2,3-diamino-6,7-dihydro-1H,5H-pyrazolo[1,2-a]pyrazol-1-one and addition salts thereof;

at least one second oxidation base chosen from para-phenylenediamine, para-tolylenediamine, and addition salts thereof; and at least one first coupler chosen from substituted meta-aminophenols of formula (II) and addition salts thereof:

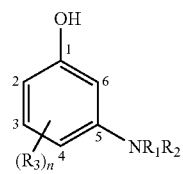

(II)

wherein:

$R_1$ and $R_2$, which may be identical or different, are chosen from hydrogen; alkyl radicals; monohydroxyalkyl radicals; polyhydroxyalkyl radicals; and monoaminoalkyl radicals; or $R_1$ and $R_2$ may form, together with the nitrogen atom to which they are attached, a saturated or unsaturated, 5- to 7-membered cyclic group comprising at least one heteroatom, which may be unsubstituted or substituted with at least one radical chosen from carboxyl, carboxamido, hydroxyl, amino, monoalkylamino, and dialkylamino radicals, and alkyl radicals optionally substituted with at least one radical chosen from hydroxyl, amino, monoalkylamino, and dialkylamino radicals;

R₃, which may be identical or different, are chosen from halogen atoms; alkyl radicals; alkoxy radicals; monohydroxyalkyl radicals; polyhydroxyalkyl radicals; monohydroxyalkoxy radicals; and polyhydroxyalkoxy radicals;

n is an integer ranging from 0 to 4;

with the proviso that when n is equal to 0, then at least one of the radicals $R_1$ and $R_2$ is not hydrogen;

wherein the at least one first coupler and the at least one first oxidation base are present in a mole ratio of greater than 1, the at least one first oxidation base and the second oxidation base are present in a mole ratio ranging from 0.5 to 1.5, and the molar amount of the first oxidation base is greater than or equal to $2.5 \times 10^{-3}$ mol per 100 g of composition.

2. The composition of claim 1, wherein $R_1$ and $R_2$, which may be identical or different, are chosen from hydrogen; alkyl radicals; and monohydroxyalkyl radicals; or $R_1$ and $R_2$ may form, together with the nitrogen atom to which they are attached, a ring chosen from pyrrolidine, piperidine, homopiperidine, piperazine, homopiperazine, and morpholine heterocycles; the rings optionally being substituted with at least one radical chosen from hydroxyl, amino, mono($C_1$-$C_2$)alkylamino, di($C_1$-$C_2$)alkylamino, carboxyl, and carboxamido radicals, and $C_1$-$C_4$ alkyl radicals optionally substituted with at least one radical chosen from hydroxyl, amino, mono($C_1$-$C_2$)alkylamino, and di($C_1$-$C_2$)alkylamino radicals.

3. The composition of claim 1, wherein $R_3$ is chosen from halogen atoms, alkyl radicals, alkoxy radicals, and monohydroxyalkoxy radicals.

4. The composition of claim 1, wherein n is an integer ranging from 0 to 2.

5. The composition of claim 1, wherein the at least one substituted meta-aminophenol of formula (II) is chosen from 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 6-chloro-2-methyl-5-aminophenol, 5-amino-2,4-dimethoxyphenol, 5-(γ-hydroxypropylamino)-2-methylphenol, 3-dimethylaminophenol; 2-methyl-5-dimethylaminophenol; 2-ethyl-5-dimethylaminophenol; 2-methoxy-5-dimethylaminophenol; 2-ethoxy-5-dimethylaminophenol; 2-(β-hydroxyethyl)-5-dimethylaminophenol; 3-diethylaminophenol; 2-methyl-5-diethylaminophenol; 2-ethyl-5-diethylaminophenol; 2-methoxy-5-diethylaminophenol; 2-ethoxy-5-diethylaminophenol; 2-(β-hydroxyethyl)-5-diethylaminophenol; 3-di(β-hydroxyethyl)aminophenol; 2-methyl-5-di(β-hydroxyethyl)aminophenol; 2-ethyl-5-di(β-hydroxyethyl)aminophenol; 2-methoxy-5-di(β-hydroxyethyl)aminophenol; 2-ethoxy-5-di(β-hydroxyethyl)aminophenol; 2-(β-hydroxyethyl)-5-di(β-hydroxyethyl)aminophenol; 3-pyrrolidin-1-ylphenol; 2-methyl-5-pyrrolidin-1-ylphenol; 2-ethyl-5-pyrrolidin-1-ylphenol; 2-methoxy-5-pyrrolidin-1-ylphenol; 2-ethoxy-5-pyrrolidin-1-ylphenol; 2-(β-hydroxyethyl)-5-pyrrolidin-1-ylphenol; 3-piperidin-1-ylphenol; 2-methyl-5-piperidin-1-ylphenol; 2-ethyl-5-piperidin-1-ylphenol; 2-methoxy-5-piperidin-1-ylphenol; 2-ethoxy-5-piperidin-1-ylphenol; 2-(β-hydroxyethyl)-5-piperidin-1-ylphenol; 3-piperazin-1-ylphenol; 2-methyl-5-piperazin-1-ylphenol; 2-ethyl-5-piperazin-1-ylphenol; 2-methoxy-5-piperazin-1-ylphenol; 2-ethoxy-5-piperazin-1-ylphenol; 2-(β-hydroxyethyl)-5-piperazin-1-ylphenol; 3-(4-methylpiperazin-1-yl) phenol; 2-methyl-5-(4-methylpiperazin-1-yl)phenol; 2-ethyl-5-(4-methylpiperazin-1-yl)phenol; 2-methoxy-5-(4-methylpiperazin-1-yl)phenol; 2-ethoxy-5-(4-methylpiperazin-1-yl)phenol; 2-(β-hydroxyethyl)-5-(4-methylpiperazin-1-yl)phenol; 3-(4-ethylpiperazin-1-yl)phenol; 2-methyl-5-(4-ethylpiperazin-1-yl)phenol; 2-ethyl-5-(4-ethylpiperazin-1-yl)phenol; 2-methoxy-5-(4-ethylpiperazin-1-yl)phenol; 2-ethoxy-5-(4-ethylpiperazin-1-yl)phenol; 2-(β-hydroxyethyl)-5-(4-ethylpiperazin-1-yl)phenol; 3-(4-(β-hydroxyethyl) piperazin-1-yl)phenol; 2-methyl-5-(4-(β-hydroxyethyl) piperazin-1-yl)phenol; 2-ethyl-5-(4-(β-hydroxyethyl) piperazin-1-yl)phenol; 2-methoxy-5-(4-(β-hydroxyethyl) piperazin-1-yl)phenol; 2-ethoxy-5-(4-(β-hydroxyethyl) piperazin-1-yl)phenol; 2-(β-hydroxyethyl)-5-(4-(β-hydroxyethyl)piperazin-1-yl)phenol; 3-morpholin-4-ylphenol; 2-methyl-5-morpholin-4-ylphenol; 2-ethyl-5-morpholin-4-ylphenol; 2-methoxy-5-morpholin-4-ylphenol; 2-ethoxy-5-morpholin-4-ylphenol; and 2-(β-hydroxyethyl)-5-morpholin-4-ylphenol.

6. The composition of claim 5, wherein the at least one substituted meta-aminophenol of formula (II) is chosen from 5-N-(β-hydroxyethylamino)-2-methylphenol, 5-amino-2-methylphenol, and 6-chloro-2-methyl-5-aminophenol.

7. The composition of claim 1, wherein the first coupler/first oxidation base mole ratio ranges from 2 to 5.

8. The composition of claim 1, wherein the first oxidation base/second oxidation base mole ratio ranges from 0.7 to 1.3.

9. The composition of claim 1, further comprising at least one additional oxidation base chosen from para-aminophenols and addition salts thereof.

10. The composition of claim 1, further comprising at least one additional coupler chosen from 2-amino-3-hydroxypyridine, 1,3-dihydroxy-2-methylbenzene, and addition salts thereof.

11. The composition of claim 1, further comprising at least one oxidizing agent.

12. A process for dyeing keratin fibers, comprising applying a dye composition to the keratin fibers in the presence of at least one oxidizing agent, for a time that is sufficient to develop a desired coloration;

wherein the dye composition comprises, in a medium suitable for dyeing:

at least one first oxidation base chosen from 2,3-diamino-6,7-dihydro-1H,5H-pyrazolo[1,2-a]pyrazol-1-one and addition salts thereof;

at least one second oxidation base chosen from para-phenylenediamine, para-tolylenediamine, and addition salts thereof; and at least one first coupler chosen from substituted meta-aminophenols of formula (II) and addition salts thereof:

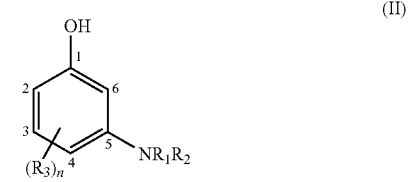

(II)

wherein:

$R_1$ and $R_2$, which may be identical or different, are chosen from hydrogen; alkyl radicals; monohydroxyalkyl radicals; polyhydroxyalkyl radicals; and monoaminoalkyl radicals; or $R_1$ and $R_2$ may form, together with the nitrogen atom to which they are attached, a saturated or unsaturated, 5- to 7-membered cyclic group comprising at least one heteroatom, which may be unsubstituted or substituted with at least one radical chosen from carboxyl, carboxamido, hydroxyl, amino, monoalkylamino, and dialkylamino radicals, and alkyl radicals optionally substituted with at least one radical chosen from hydroxyl, amino, monoalkylamino, and dialkylamino radicals;

$R_3$, which may be identical or different, are chosen from halogen atoms; alkyl radicals; alkoxy radicals; monohydroxyalkyl radicals; polyhydroxyalkyl radicals; monohydroxyalkoxy radicals; and polyhydroxyalkoxy radicals;

n is an integer ranging from 0 to 4;

with the proviso that when n is equal to 0, then at least one of the radicals $R_1$ and $R_2$ is not hydrogen;

wherein the at least one first coupler and the at least one first oxidation base are present in a mole ratio of greater than 1, the at least one first oxidation base and the at least one second oxidation base are present in a mole ratio ranging from 0.5 to 1.5, and the molar amount of the first oxidation base is greater than or equal to $2.5 \times 10^{-3}$ mol per 100 g of composition.

13. A multi-compartment device, comprising at least one first compartment containing a dye composition and at least one second compartment containing at least one oxidizing agent;

wherein the dye composition comprises, in a medium suitable for dyeing:

at least one first oxidation base chosen from 2,3-diamino-6,7-dihydro-1H,5H-pyrazolo[1,2-a]pyrazol-1-one and addition salts thereof;

at least one second oxidation base chosen from para-phenylenediamine, para-tolylenediamine, and addition salts thereof; and at least one first coupler chosen from substituted meta-aminophenols of formula (II) and addition salts thereof:

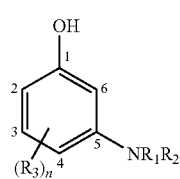

(II)

wherein:

$R_1$ and $R_2$, which may be identical or different, are chosen from hydrogen; alkyl radicals; monohydroxyalkyl radicals; polyhydroxyalkyl radicals; and monoaminoalkyl radicals; or $R_1$ and $R_2$ may form, together with the nitrogen atom to which they are attached, a saturated or unsaturated, 5- to 7-membered cyclic group comprising at least one heteroatom, which may be unsubstituted or substituted with at least one radical chosen from carboxyl, carboxamido, hydroxyl, amino, monoalkylamino, and dialkylamino radicals, and alkyl radicals optionally substituted with at least one radical chosen from hydroxyl, amino, monoalkylamino, and dialkylamino radicals;

$R_3$, which may be identical or different, are chosen from halogen atoms; alkyl radicals; alkoxy radicals; monohydroxyalkyl radicals; polyhydroxyalkyl radicals; monohydroxyalkoxy radicals; and polyhydroxyalkoxy radicals;

n is an integer ranging from 0 to 4;

with the proviso that when n is equal to 0, then at least one of the radicals $R_1$ and $R_2$ is not hydrogen;

wherein the at least one first coupler and the at least one first oxidation base are present in a mole ratio of greater than 1, the at least one first oxidation base and the at least one second oxidation base are present in a mole ratio ranging from 0.5 to 1.5, and the molar amount of the at least one first oxidation base is greater than or equal to $2.5 \times 10^{-3}$ mol per 100 g of composition.

14. The process of claim 12, wherein coloration is obtained on natural or permanent-waved grey hair containing 90% white hairs having, according to the CIELab notation, a value for L* of less than or equal to 50, a value for a* ranging from 10 to 25, a value for b* ranging from 3 and 25, and a ratio b*/a* ranging from 0.3 to 1.

* * * * *